(12) United States Patent
Levy

(10) Patent No.: US 10,420,646 B2
(45) Date of Patent: Sep. 24, 2019

(54) SHOULDER PROXIMAL CENTRALIZER AND METHOD TO USE THE SAME

(71) Applicant: Orthopaedic Consultants of South Florida, Inc., Fort Lauderdale, FL (US)

(72) Inventor: Jonathan Levy, Fort Lauderdale, FL (US)

(73) Assignee: Orthopaedic Consultants of South Florida, Inc., Fort Lauderdale, FL (US)

( * ) Notice: Subject to any disclaimer, the term of this patent is extended or adjusted under 35 U.S.C. 154(b) by 236 days.

(21) Appl. No.: 15/481,326

(22) Filed: Apr. 6, 2017

(65) Prior Publication Data

US 2017/0209275 A1    Jul. 27, 2017

Related U.S. Application Data

(63) Continuation of application No. PCT/US2015/054940, filed on Oct. 9, 2015.

(60) Provisional application No. 62/062,706, filed on Oct. 10, 2014.

(51) Int. Cl.
*A61F 2/40* (2006.01)
*A61F 2/30* (2006.01)

(52) U.S. Cl.
CPC ........ *A61F 2/30724* (2013.01); *A61F 2/4059* (2013.01); *A61F 2002/30736* (2013.01)

(58) Field of Classification Search
CPC .... A61F 2/4059; A61F 2/4612; A61F 2/4607; A61F 2/4614; A61B 17/8808
See application file for complete search history.

(56) References Cited

U.S. PATENT DOCUMENTS

| 5,746,771 A * | 5/1998 | Clement, Jr. ...... A61B 17/1659 |
| | | 623/23.22 |
| 6,283,999 B1 | 9/2001 | Rockwood, Jr. |
| 2003/0109933 A1* | 6/2003 | Weissman .......... A61B 17/8808 |
| | | 623/23.22 |
| 2009/0105838 A1 | 4/2009 | Russo et al. |
| 2009/0265010 A1 | 10/2009 | Angibaud et al. |

(Continued)

FOREIGN PATENT DOCUMENTS

| DE | 19848476 C1 * | 8/2000 | ......... A61B 17/8808 |
| EP | 1269937 A2 | 1/2003 | |

(Continued)

OTHER PUBLICATIONS

Translation of DE19848476 retrieved from espacenet on Jan. 22, 2019 (Year: 2019).*

(Continued)

*Primary Examiner* — Megan Y Wolf
(74) *Attorney, Agent, or Firm* — Veros Legal Solutions, LLP

(57) ABSTRACT

A method and apparatus for proper sizing and centralization of a shoulder humerus implant are provided. The method and apparatus replicate the proper stem height and position for a shoulder humerus implant, and may be used during trialing and maintaining the proper height and orientation during implantation. The apparatus further assists in maintaining the shoulder humerus implant stem at the center of the humeral canal to allow for proper cementing technique, and facilitates selection of the appropriate humeral head replacement.

15 Claims, 1 Drawing Sheet

(56) References Cited

U.S. PATENT DOCUMENTS

2011/0282349 A1 11/2011 Acker et al.
2013/0261755 A1 10/2013 Anthony et al.

FOREIGN PATENT DOCUMENTS

WO 2011023921 A1 3/2011
WO 2011138090 A1 11/2011

OTHER PUBLICATIONS

Extended European Search Report issued in EP 15849083.9 dated Jul. 4, 2018.

* cited by examiner

SHOULDER PROXIMAL CENTRALIZER AND METHOD TO USE THE SAME

CROSS-REFERENCE TO RELATED APPLICATIONS

This application is a continuation application of International Application No. PCT/US2015/054940, filed on Oct. 9, 2015, which claims priority to U.S. Provisional Patent Application Ser. No. 62/062,706, which was filed on Oct. 10, 2014, the entire contents of which is hereby incorporated by reference.

BACKGROUND OF THE INVENTION

Field of the Invention

Disclosed herein is an apparatus and method for implantation of a shoulder humerus implant. In particular, the device offers a simple to use surgical instrument to set the height for proper placement of the shoulder humerus implant, to centrally locate the stem for proper cement technique, and provide implant size information based on the boney anatomy of a patient. Methods of using the device are likewise provided.

Description of the Related Technology

A proximal humerus fracture is a common injury to the shoulder. Especially common in elderly individuals due to osteoporosis, proximal humerus fractures are among the most common broken bones in the shoulder. In patients older than sixty five, proximal humerus fractures are the third most common broken bone after hip fractures and wrist fractures.

A proximal humerus fracture occurs when the ball, of the ball-and-socket shoulder joint, is broken and can pose significant challenges to the patient as treatment can be very limiting and the outcomes are often fair or poor. Many patients who sustain this injury do not regain full strength or mobility of the shoulder.

A humerus is a long bone in the arm running from the shoulder to elbow, connecting the scapula to the radius and ulna. The humerus is divided into the proximal humerus, the humeral shaft, and the distal humerus. The components of the proximal humerus are called the humeral head (the ball of the shoulder), the tubercles (the greater and lesser tubercles), with the tubercles extending into the humeral shaft. The tubercles are adjacent to the ball, and rotator cuff muscles attach to the tubercles.

Treatment for a proximal humerus fracture when the bone is displaced may require surgery to realign or replace the damaged bone fragments. Additionally, surgical treatment may require securing the realigned bone fragments in position with metal implants. Another option is to replace the humerus with a prosthetic humerus implant.

During surgery to replace the humerus, the implant may not be properly centralized in the humeral canal. The implant's height may not be suitable for the patient's boney anatomy. The humerus head size may not be properly determined. There remains a need for improved devices and methods of surgery in humeral implant placement, to promote proper alignment of the humeral implant, and to promote proper sizing of the humeral implant.

SUMMARY

The present invention relates to an apparatus and method for completing a shoulder humerus implant placement in surgery.

An apparatus in fan-like shape mates with a shoulder humerus implant to provide appropriate height to the implant, provide information on shoulder humerus implant centralization, and provide information on the patient's boney anatomy and humeral head size.

The apparatus has a head in substantially half-moon shape, which has an attachment hole or a male attachment mechanism. A mid-panel separates the attachment hole and a visualization window. Located on and at approximately the central point of the mid-panel is an anti-rotation pin. The visualization window area is maximized for better visualization. A distal end panel with two portions having a first height and a second height is situated distally from the head and adjacent to the visualization window. The first height comprises the lip, and the second height comprises the outer portion of the distal end panel.

In use of the invention, a surgeon mates the attachment hole with a stem neck on a shoulder humerus implant, or the male attachment mechanism with a receptive female hole on the shoulder humerus implant, then mates the anti-rotation pin with a receptive hole on the shoulder humerus implant. The lip height provides additional height to the shoulder humerus implant, which allows surgeons to set the proper height and maintain the proper height during implantation. The shoulder proximal centralizer maintains the humeral stem in the center of the prepared humeral canal to allow for proper fixation and cement technique.

The shoulder proximal centralizer also serves as an estimate of the humeral head size. The shoulder proximal centralizer radius from the head to the outer panel fits with the dimension from the taper to the rim of the bone, where the shoulder proximal centralizer sits. This dimension is also the dimension of the proper humeral head size, and provides an estimate for the proper humeral head implant choice.

DETAILED DESCRIPTION OF CERTAIN INVENTIVE EMBODIMENTS

Embodiments of this application relate to a shoulder proximal centralizer to be used in conjunction with a shoulder humerus implant during surgery. The shoulder proximal centralizer stabilizes the shoulder humerus implant, provides a visualization window to check the shoulder humerus implant's location in the humeral canal of the patient, assists in sizing of the proper humeral head, and establishes proper height of the shoulder humerus implant.

Figure 1:
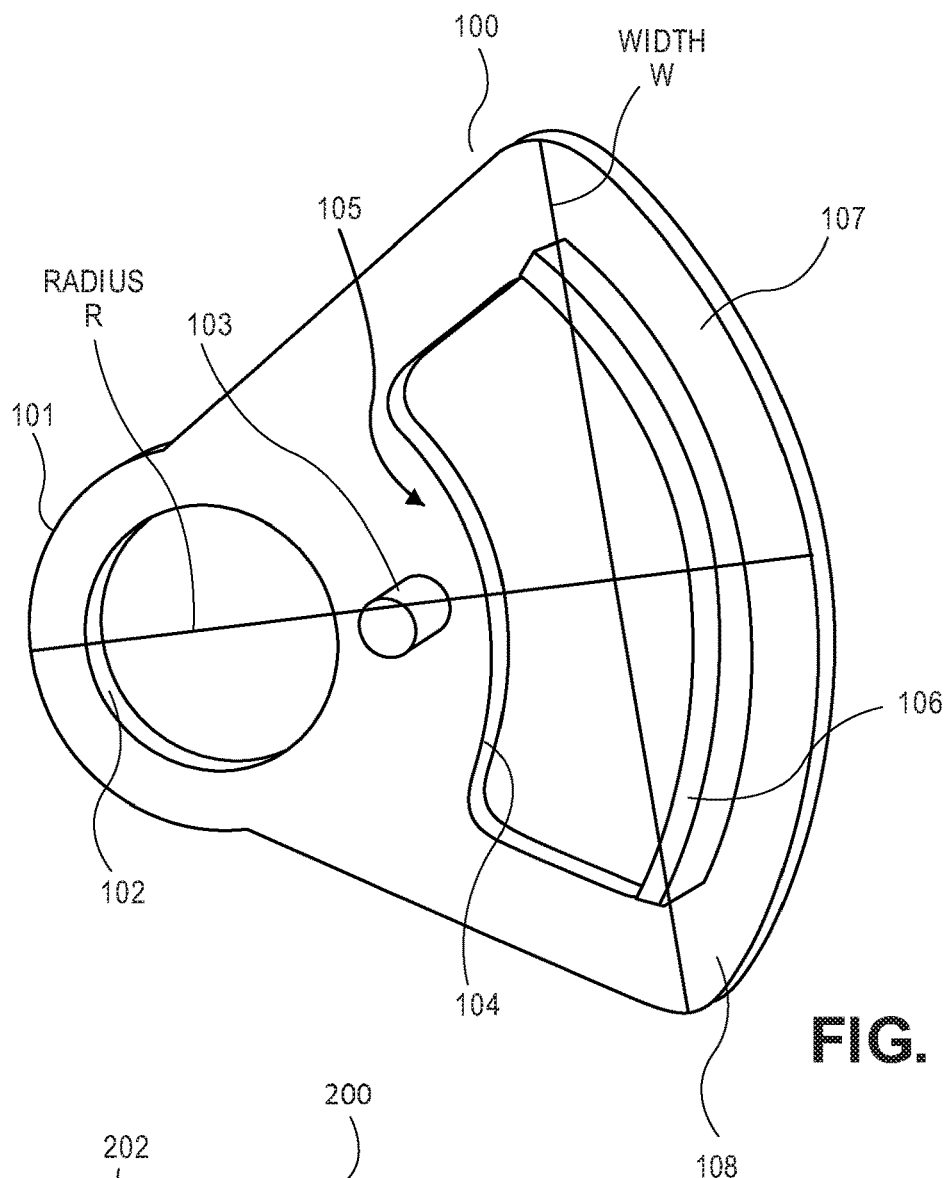
FIG. 1 is a perspective view of one embodiment of a shoulder proximal centralizer as described herein.

FIG. 1 illustrates a perspective view of the shoulder proximal centralizer 100. The shoulder proximal centralizer 100 generally has a fan-like shape body with a defined first radius R extending from the head 101 to the outer diameter 107, which is the outermost portion of the shoulder proximal centralizer 100.

Figure 2:
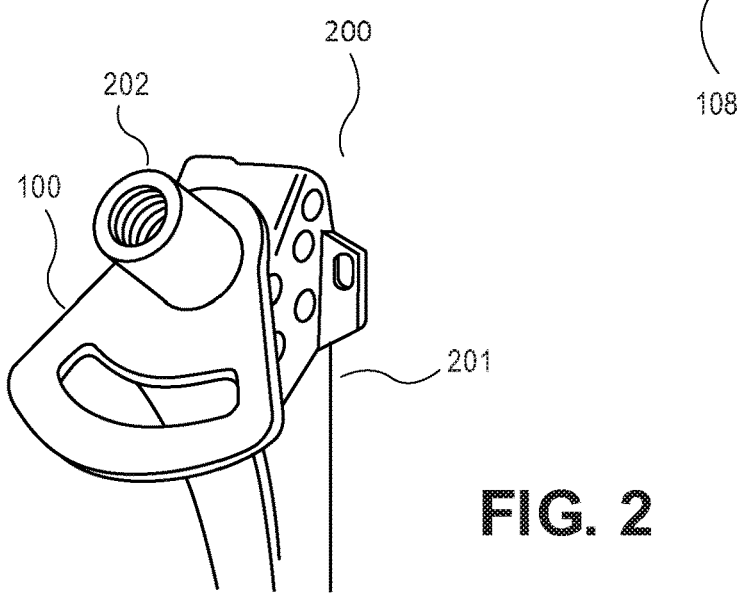
FIG. 2 illustrates a shoulder proximal centralizer in communication with a humeral stem of a shoulder humerus implant.

FIG. 2 illustrates a shoulder humerus implant 200 with a shoulder proximal centralizer 100 in place. A shoulder humerus implant 200 replaces a human humerus where fractures are severe such that stabilizer implants are not recommended. A shoulder humerus implant 200 generally comprises a stem 201, which fits into the humeral canal during implantation and a stem neck 202, which is cemented into place, and a humerus head implant (not shown).

The shoulder humerus implant 200 is chosen to fit the patient's size, but accurate sizing and placement during implantation remains a challenge. The shoulder proximal centralizer 100 aims to solve this problem, together with location issues and boney anatomy information collection during shoulder humerus surgery.

A shoulder humerus implant 200 is illustrated in FIG. 2 while mating with the shoulder proximal centralizer 100. The shoulder humerus implant 200 is an implant used to support a humeral head replacement and facilitate repair of the large and small tubercles. As illustrated in FIG. 2, the shoulder humerus implant 200 comprises a stem 201 and a stem neck 202 located at the proximal end, upon which the shoulder proximal centralizer 100 attaches.

The stem 201 of the shoulder humerus implant 200 is generally in cylindrical shape with a head to mimic the head of the humerus. The stem neck 202 is located at the top of the implant and mates with head. The shoulder humerus implant 200 size, location in the humeral canal, and fitness with the patient's boney anatomy are of importance to surgery success. The shoulder proximal centralizer 100 aims to improve these features.

Returning to FIG. 1, at the edge of the shoulder proximal centralizer 100 is the head 101. The head 101 of the shoulder proximal centralizer 100 is generally in half moon shape with a separate, smaller second radius r (not shown). The head's 101 half-moon shape is to accommodate the attachment hole 102 shape, even though the attachment hole 102 may be of other shapes. A half-moon shape for the head 101 also minimizes any sharp corners, which may be undesirable for an apparatus to be used in a surgery environment. Sharp corners may increase the risk of tear and cut to surrounding tissues during use. A half-moon shape also facilitates better visualization of the greater and lesser tuberosity position when preparing for repair.

On the head 101 of the shoulder proximal centralizer 100 and centrally located is an attachment hole 102. Preferably, the attachment hole 102 is in a shape that may be attached or mated with the shoulder humerus implant's stem neck 202. FIGS. 1 and 2 show the attachment hole 102 in round shape, however, it is to be appreciated that the attachment hole 102 may be in other shapes suitable to mate with the shape of the stem neck 202. The attachment hole 102 is preferably centrally located to ensure symmetrical placement of the shoulder proximal centralizer 100, which promotes proper use of the visualization window 104 and provides accurate information on the patient's boney anatomy, as well as assists in proper sizing of the humeral head implant.

In another embodiment, the head of the shoulder proximal centralizer has a male attachment mechanism to mate with a receptive female hole on the head of the shoulder humerus implant. This embodiment is not shown in the Figures, and thus no reference to numerals is made in this description. The male attachment mechanism generally extends from the head in the same direction with the anti-rotation pin. The male attachment mechanism may be in cylindrical, square block, or rectangular block shape, or any other shape to mate with the receptive female hole on the shoulder humerus implant. The male attachment mechanism may be sized to fit with the receptive female hole, and is preferably with sufficient height to provide secure attachment for the shoulder proximal centralizer. At the same time, the male attachment mechanism height is preferably not too large, which may impedes removal during surgery.

Extending from the head 101 is the body of the shoulder proximal centralizer 100, in a fan-like shape with an outer diameter 107 forming a part-circle. The body of the shoulder proximal centralizer 100 houses part of the attachment hole 102 or the male attachment mechanism, the mid-panel 105, the visualization window 104, and the distal end panel 108.

Adjacent to the attachment hole 102 is a mid-panel 105. The mid-panel 105 shape is general defined by the head 101 and the visualization window 104. The mid-panel 105 area is sized to provide structural stability to the shoulder proximal centralizer 100, and also to provide support for and house the anti-rotation pin 103. The mid-panel 105 is located, generally, at the mid-point of the shoulder proximal centralizer 100 as defined by the radius R, between the head 101 and the visualization window 104. However, the mid-panel 105 does not necessarily need to be located at the mid-point of the first radius R extending from the head 101 to the outer diameter 107, and may vary in location on the first radius R, such that the distance between the mid-panel 105 to the head 101 and the distance between the mid panel 105 to the outermost point of the outer diameter 107 may not be equal. The mid-panel 105 only needs to be located between the attachment hole 102 and the visualization window 104.

According to embodiments, the anti-rotation pin 103 is located on the mid-panel 105, at approximately the center point of the mid-panel 105. The anti-rotation pin 103 is sized to match a mating hole located on the shoulder humerus implant 200. Depending on the shape of the mating hole on the shoulder humerus implant 200, the anti-rotation pin 103 may be in cylindrical, square block, rectangular block, or any other suitable shapes to mate with the hole on the shoulder humerus implant 200.

The sizes of the anti-rotation pin 103 and its corresponding mating hole are preferably large enough to provide support and fixation for the shoulder proximal centralizer 100 during use, but at the same time small enough so as to not affect the structural strength of the shoulder humerus implant 200. Moreover, the height of the anti-rotation pin 103 is such that adequate support and fixation is provided, but the height is also chosen to prevent extensive movement of the shoulder proximal centralizer 100 during installation and removal. If the anti-rotation pin's 103 height is too large, extended upward movement of the shoulder proximal centralizer 100 will be required to remove the anti-rotation pin 103 from the receptive hole, which is not preferred in a congested surgery environment.

Adjacent to the mid-panel 105 is the visualization window 104. The visualization window 104 is located distally from the head 101, and in between the mid-panel 105 and the distal end panel 107. The visualization window 104 provides a window for viewing the shoulder humerus implant 201 as implanted in the humeral canal. The shoulder humerus implant 200 is placed in the humeral canal during implantation, and the visualization provides information on centralization of the shoulder humerus implant 200. If the shoulder humerus implant 200 is not centrally located, a different sized shoulder proximal centralizer 100 can be selected until the shoulder humerus implant 200 is centrally located.

According to embodiments, the visualization window 104 is preferably sized and shaped to maximize the viewing area. The viewing area is thus of curved rectangular shape to maximize the viewing area, as seen in FIG. 1. The visualization window 104 may alternatively be of other shapes, e.g. round, square, rectangular, which may enable visualization. The viewing area is also sized to ensure adequate structural strength of the shoulder proximal centralizer 100 as a whole. If the viewing area is too large, there may not be adequate structural support for the shoulder proximal centralizer 100.

Adjacent to the visualization window 104 and distal from the head 101 is the distal end panel 108, which defines the end of the shoulder proximal centralizer 100. The distal end panel 108 comprises two different heights, the first height is taller than the second height. The first height is adjacent to the visualization window 104 and is termed the "lip" 106. The lip's 106 height sets the height of the shoulder humerus implant stem 201, estimates the proper humeral head size, and centralizes the shoulder humerus implant stem 201 in the humeral canal.

The second portion of the distal panel 108 has a second height and defines the end of the shoulder proximal implant 100. The second portion extends distally and radially from the head 101, with an outer diameter 107 to match the size of the proper humeral head. The second portion of the distal panel 105 is sized such that the shoulder proximal centralizer width W at the distal end panel matches the largest width of the shoulder humerus implant 200 proximal end, upon which the shoulder proximal centralizer 100 mates. The distal end panel has a lip with a first thickness and an outer end with a second thickness, the first thickness being greater than the second thickness.

The edges of the distal end panel 108 are preferably rounded to as to avoid tear or cut injuries to surrounding tissues and facilitate visualization while the shoulder proximal centralizer 100 is in use. It is contemplated that the shoulder proximal centralizer 100 comes into contact with the patient's surrounding tissues during use, and thus the shoulder proximal centralizer 100 is configured to reduce the incidences of unnecessary tear or cut to such surrounding tissues.

The shoulder proximal centralizer 100 is preferably made of metal, e.g. stainless steel, or plastic. The shoulder proximal centralizer 100 may be made of hypo-allergenic materials to be used in patients with known allergies. The shoulder proximal centralizer is made in a variety of radius R, such that one with suitable dimensions may be selected by the surgeon for use during surgery. Typically, a variety of shoulder proximal centralizers with various dimensions are made available during surgery. The radius R may be between 20 millimeters to 60 millimeters, but may be more or less to fit the patient's boney anatomy.

In use of the invention, a shoulder humerus implant 200 is placed in a human patient humeral canal during surgery. Generally, conventional placement of the shoulder humerus implant 200 is difficult because it does not provide adequate information on height, size, and location of the implant relative to the humeral canal and greater and lesser tubercles. The shoulder proximal centralizer 100 as disclosed herein overcomes many of these difficulties by providing enhanced visualization, placement, sizing, and centralization of an implant in a patient. More particularly, the shoulder proximal centralizer 100 mates with the shoulder humerus implant stem neck 202 and provides height information, humeral head size information, centralization viewing, and boney anatomy information.

The shoulder proximal centralizer 100 is placed to mate the attachment hole 102 with the shoulder humerus implant stem neck 202 by sliding from the distal end to the proximal end of the stem neck 202. The anti-rotation pin 103 (not shown in FIG. 2) mates with a hole on the shoulder humerus implant stem 201.

Alternatively, when the shoulder humerus implant has a female mating hole in place of the stem neck, a shoulder proximal centralizer having a male attachment mechanism may be used. The shoulder proximal centralizer is placed to mate the male attachment mechanism with a female receptive hole on the shoulder humerus implant 200. The anti-rotation pin 103 is placed to mate with another receptive hole on the shoulder humerus implant 200.

A properly sized shoulder proximal centralizer is one where the lip 106 sits on the non-fractured portion of the humerus. The lip 106 similarly sets the height of the stem 201 by the first height. The properly sized humeral head may then be placed onto the humerus implant stem neck 202 for estimation of proper greater and lesser tubercle positioning. If the distal end panel 108 of the shoulder proximal centralizer 100 does not rest on the rim of the proximal humerus, the shoulder proximal centralizer 100 may be replaced with a different size shoulder proximal centralizer.

A person may view the shoulder humerus implant stem 201 position through the visualization window 104 after the shoulder proximal centralizer 100 has been in place and mated with the shoulder humerus implant stem neck 202. If the shoulder humerus implant stem 201 is not centrally located in the humeral canal, the shoulder humerus implant stem 201 may be adjusted until centralization is achieved or an alternative sized shoulder proximal centralizer 100 may be selected.

The lip 106 height provides information on implant fitness with the patient's boney anatomy. For example, a shoulder humerus stem 201 which fits centrally in the humeral canal with a shoulder proximal centralizer 100 situated at the stem neck 202 predicts the proper height position of the stem 201, avoids malposition of the shoulder humerus stem within the canal of the humerus, and accurately predicts the proper humeral head size and diameter. On the other hand, if the shoulder proximal centralizer 100 is unable to fit onto the stem neck 202 and humeral rim bone properly, the implant height may be inaccurately estimated and an adjustment of the shoulder humerus stem 201 height is necessary. Furthermore, if the shoulder proximal centralizer 100 fits onto the stem neck 202 but not onto the humeral rim bone properly, an alternative shoulder proximal centralizer with a different radius R can be selected and/or the surgeon is alerted to check the stem 201 and ensure that it is centrally placed in the humeral bone.

The radius R of a properly fitted shoulder proximal centralizer 100 may be used to estimate the proper size of the humeral head, thereby enabling proper choice of humeral head implants. The distance from the center point of the attachment hole 102 to the outer diameter 107 is approximately the radius of the properly fitted humeral head implant. The shoulder proximal centralizer 100 thus gives information on the patient's boney anatomy upon use with a shoulder humerus implant 200. A different sized shoulder humerus implant 200 or humeral head implant may be chosen based on information provided by the shoulder proximal centralizer 100.

Additional adjustment of the shoulder humerus implant 200 to centralize the implant 200 in the humeral canal may be required. Once a shoulder humerus implant 200 of the appropriate size has been properly situated, and information on the proper humeral head size and shoulder humerus implant has been determined, the shoulder humerus implant 200 may be fixed and cemented into place, utilizing the shoulder proximal centralizer 100 during the cementation process to replicate proper positioning of the humerus stem 201. Thereafter, the shoulder proximal centralizer 100 may be removed from the stem neck 202.

Replacement humeral head implant may be attached to the shoulder humerus implant to complete the therapy. Humeral head implant is selected based on size estimation provided by the shoulder proximal centralizer 100 as above.

Variations and modifications will occur to those of skill in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implements.

Examples of changes, substitutions, and alterations are ascertainable by one skilled in the art and could be made without departing from the scope of the information disclosed herein. All references cited are hereby incorporated by reference herein in their entireties and made part of this application.

What is claimed is:

1. A shoulder proximal centralizer, comprising:
    a head wherein an attachment hole is located, the attachment hole is sized to match a stem neck of a shoulder humerus implant;
    a body extending from the head to an outer diameter to form a fan-like shape with a defined radius between 20 millimeters to 60 millimeters extending from the head to the outer diameter;
    a visualization window located towards a distal end of the body for visualization during surgery;
    a mid-panel separating the attachment hole and the visualization window, wherein an anti-rotation pin is located to mate with a shoulder humerus implant during use; and
    a distal end panel having a lip with a first thickness, and an outer end with a second thickness, the first thickness is greater than the second thickness.

2. The shoulder proximal centralizer of claim 1, wherein the head is in substantially a half-moon shape.

3. The shoulder proximal centralizer of claim 1, wherein the attachment hole has a round shape.

4. The shoulder proximal centralizer of claim 1, wherein the attachment hole is centralized on the head.

5. The shoulder proximal centralizer of claim 1, wherein the anti-rotation pin is located at approximately a middle point of the mid panel.

6. The shoulder proximal centralizer of claim 1, wherein the anti-rotation pin is in a cylindrical shape.

7. The shoulder proximal centralizer of claim 1, wherein the anti-rotation pin is in a square block shape.

8. The shoulder proximal centralizer of claim 1, wherein the anti-rotation pin is in a rectangular block shape.

9. The shoulder proximal centralizer of claim 1, wherein the shoulder proximal centralizer is made of plastic material.

10. The shoulder proximal centralizer of claim 1, wherein the shoulder proximal centralizer is made of stainless steel.

11. The shoulder proximal centralizer of claim 1, wherein the shoulder proximal centralizer is made of a hypo-allergenic material.

12. A method to stabilize a shoulder humerus implant during surgery, the method comprising:
    placing a shoulder humerus implant having a stem neck in a humeral canal of a patient;
    providing a first shoulder proximal centralizer of claim 1;
    placing the first shoulder proximal centralizer onto the shoulder humerus implant by mating the attachment hole of the first shoulder proximal centralizer with the stem neck of the shoulder humerus implant;
    mating the anti-rotation pin on the first shoulder proximal centralizer with a receptive hole on the shoulder humerus implant;
    resting the lip of the first shoulder proximal centralizer on a non-fractured portion of the humerus;
    wherein the lip establishes a proper shoulder humerus implant height; and
    wherein a first shoulder humerus implant stem position is stabilized in the humeral canal of the patient.

13. The method of claim 12, further comprising the steps of:
    determining a proper size of a humeral head; and
    determining the proper height of the shoulder humerus implant; and
    if the first shoulder proximal centralizer distal end panel does not rest on a rim of the proximal humerus, replacing the first shoulder proximal centralizer with a second shoulder proximal centralizer with a different radius than the first shoulder proximal centralizer.

14. The method of claim 12, further comprising the steps of:
    viewing the shoulder humerus implant position in the humeral canal through the visualization window on the shoulder proximal centralizer;
    determining whether the shoulder humerus implant is centrally situated in the humeral canal of the patient; and
    if the shoulder humerus implant is not centrally situated in the humeral canal of the patient, adjusting the shoulder humerus implant position to be centrally situated in the humeral canal.

15. The method of claim 12, further comprising the steps of:
    cementing the shoulder humerus implant in the humeral canal; and removing the first shoulder proximal centralizer.

* * * * *